Jan. 1, 1974 F. A. GILBERT Plant Pat. 3,420
APPLE TREE
Filed Sept. 20, 1971
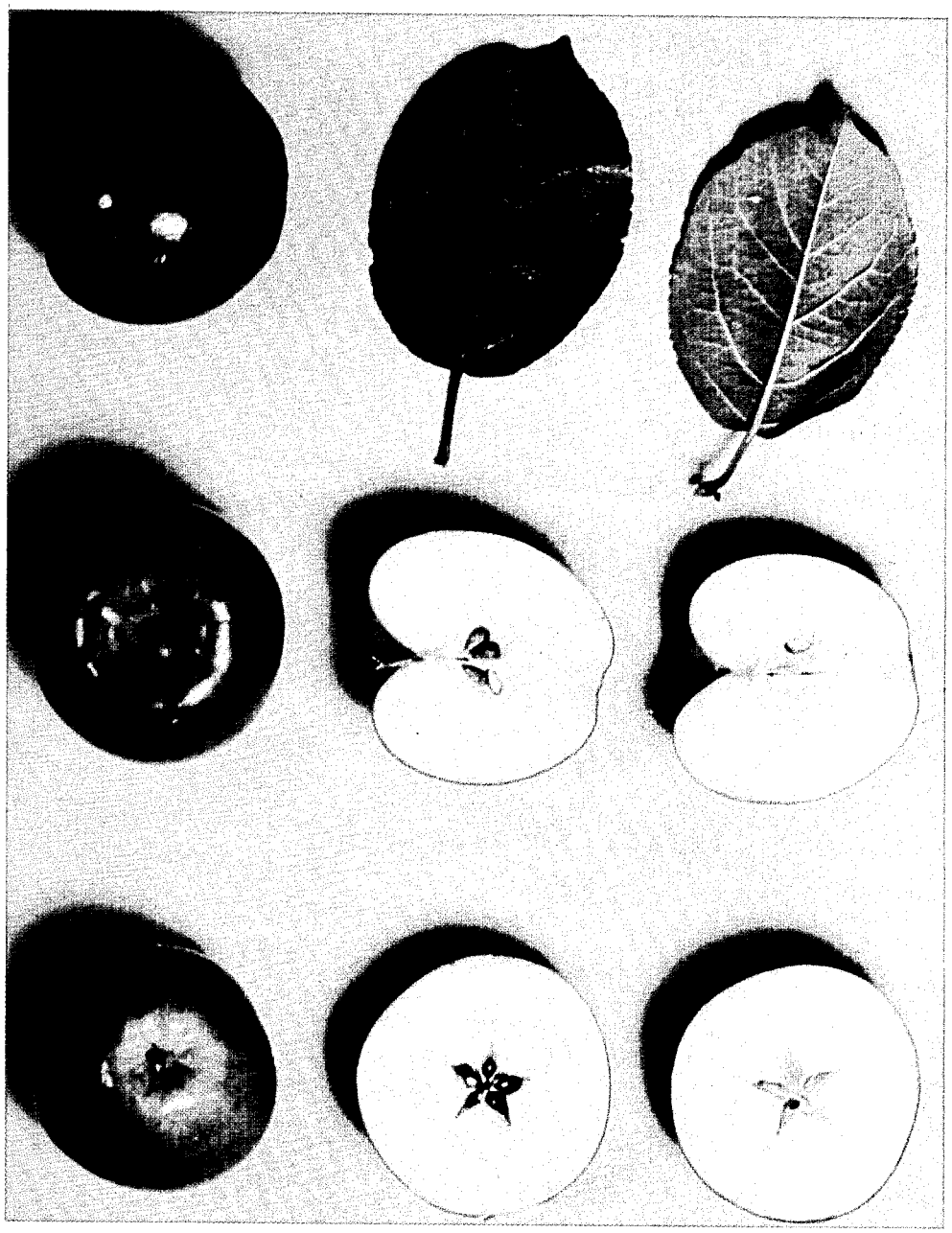
INVENTOR:
FRANKLIN A. GILBERT
ATTORNEY:
J. M. Kesbitt

United States Patent Office

Plant Pat. 3,420
Patented Jan. 1, 1974

3,420
APPLE TREE

Franklin Andrew Gilbert, 403 W. Pine St., Sturgeon Bay, Wis. 54235

Filed Sept. 20, 1971, Ser. No. 182,271
Int. Cl. A01h *5/03*
U.S. Cl. Plt.—34 1 Claim

This invention is a new and distinct variety of apple tree discovered at the Peninsular Branch Experiment Station, University of Wisconsin, Route 2, Sturgeon Bay, Wisc., in 1963. The tree is a seedling of known parentage planted in 1958. In the experiment station orchard the tree was discovered in Field K in Row 9 and was the fifth tree in the row having the progeny designation 1033, and I have named the apple variety Viking.

Viking was developed by crossing the New Jersey Selection 148849 (seed parent) and the Indiana Selection 187–4 (pollen parent) n 1956. The complete pedigree is:

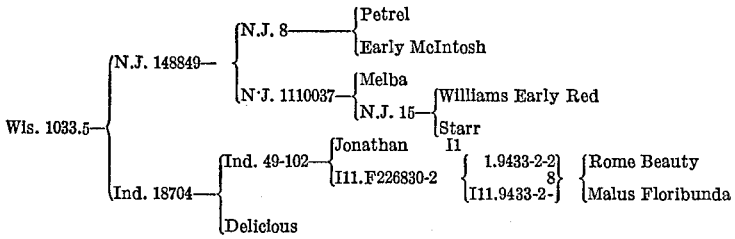

Viking has been asexually reproduced by top-working on Hibernal and Beacon trees. The grafted material has retained all of the described characteristics after propagation.

The drawing herein (color photograph) shows typical specimens of the foliage and fruit of Viking as nearly true as it is reasonably possible with the foliage specimens depicting both the upper and lower surfaces of the leaves, and the fruit depicting both the exterior (transverse and longitudinal) and interior (transverse and longitudinal) details of the fruit.

The following is a detailed description of this new variety, with the color designations according to the Nickerson Color Fan except where general color terms of ordinary dictionary significance are obvious.

Locality where grown and observed: Sturgeon Bay, Wisconsin.

Tree: Medium size; upright; spreading; vigorous; productive.

Bloom period: Blooms approximately one day earlier than McIntosh (unpatented).

Fruit:

*Shape.*—Ovate (to somewhat oblong—smaller fruits).

*Form.*—Uniform; regular; symmetrical.

*Size*—Variable—above medium. Ex. transverse diameter: 2¾", 2½", 3¼". Axial diameter: 2⅝", 2⅜", 2⅞".

*Cavity.*—Acute. Depth ½" (approximately). Width ¾" (approximately). Color—greenish; occasionally slight, smooth russet.

*Basin.*—Width: medium, ⅝"–¾" Depth: shallow, ¼"–⅜". Sides: sloping. Surface: furrowed.

*Stem.*—Length—¾"–1" (long). Thickness—medium 1/16"–3/32". Pubescent.

*Calyx.*—Lobes—persistent, recurved; outer and inner surface—pubescent, broadly lanceolate, about 3/32"–¼" long. Closed to slightly open.

*Skin.*—Very smooth, waxy with inconspicuous very small whitish dots most numerous at the calyx and surface color (Nickerson Color Fan): Darkest red 3.5 R Hue 3 Chroma 7; lightest red 5.0 Hue 4 Chroma 12; ground color (Nickerson Color Fan): 8.5 YR Hue 8 Chroma 8 to 2.5 Y Hue 8 Chroma 12. General color effect—bright glossy washed red (74–95%). Bruising—relatively tough, does not bruise easily.

*Flesh.*—Juicy. Color—white with slight pink color near calyx tube and cortex near skin in over-mature fruits. Texture—tender, fine grained. Flavor—subacid. Aroma—aromatic when left at room temperature. Quality—very good for apple of this season.

*Core.*—Median. Bundle area (longitudinal section) broadly ovate; symmetrical; halves of area equal; bundles moderately conspicuous, yellow-green. Core lines—clasping. Calyx tube—pubescent, cone to funnel shaped, stamens marginal, styles persistent. Carpels—oblate, symmetrical, axial, smooth. Seeds—acute; brown at maturity, averaged 7–10 seeds per fruit (1968), none observed with more than 2 per carpel.

Maturity season: August 20–25 (approximately 5 weeks before McIntosh [unpatented]).

Use: Dessert.

Keeping quality: At least 5–6 weeks in conventional refrigerated storage.

In particular, the Viking apple is distinguished by its early season (5 weeks before McIntosh), excellent red color; waxy finish; very good dessert quality; ability to remain on the tree until maturity; and the relatively long storage and shelf life for an apple classified as a summer apple.

I claim:

1. A new and distinct variety of apple tree substantially as described and illustrated in the foregoing specification and drawing.

No references cited.

ROBERT E. BAGWILL, Primary Examiner